(12) United States Patent
Lin et al.

(10) Patent No.: US 7,521,203 B2
(45) Date of Patent: Apr. 21, 2009

(54) FEEDING PROCESSES FOR FERMENTATION

(75) Inventors: WengLong Roy Lin, Rockville, MD (US); Firoz Rustom Mistry, Chapel Hill, NC (US); Arun Narayanaswamy Tholudur, Longmont, CO (US); Edward Todd Sorensen, Raleigh, NC (US); Wan-Seop Kim, Morrisville, NC (US); Dana Perrin, Cary, NC (US)

(73) Assignee: N.V. Organon, Oss (NL)

( * ) Notice: Subject to any disclaimer, the term of this patent is extended or adjusted under 35 U.S.C. 154(b) by 266 days.

(21) Appl. No.: 11/123,715

(22) Filed: May 6, 2005

(65) Prior Publication Data

US 2005/0202525 A1 Sep. 15, 2005

Related U.S. Application Data

(62) Division of application No. 10/292,064, filed on Nov. 12, 2002, now Pat. No. 6,955,892.

(51) Int. Cl.
*G06F 19/00* (2006.01)
*G01N 33/48* (2006.01)
*G01N 33/50* (2006.01)
*C12P 1/00* (2006.01)

(52) U.S. Cl. ................. 435/41; 435/813; 435/818
(58) Field of Classification Search ........... 435/41, 435/813, 818
See application file for complete search history.

(56) References Cited

U.S. PATENT DOCUMENTS

| | | | | |
|---|---|---|---|---|
| 4,302,542 | A | * 11/1981 | Hitzman | ............ 435/161 |
| 5,324,442 | A | * 6/1994 | Mathews | ............ 252/70 |
| 5,595,905 | A | 1/1997 | Bishop et al. | |
| 5,639,658 | A | 6/1997 | Drobish et al. | |
| 5,955,323 | A | * 9/1999 | Chen | ............ 435/91.1 |
| 6,025,169 | A | 2/2000 | Nakamura et al. | |
| 6,197,573 | B1 | 3/2001 | Suryanarayan et al. | |
| 6,284,453 | B1 | 9/2001 | Siano | |
| 2002/0039758 | A1 | 4/2002 | De Laat | |

FOREIGN PATENT DOCUMENTS

DE 297 444 A5 1/1992
EP 0 156 176 2/1985

OTHER PUBLICATIONS

Ho et al. 1999. Growth and Carotenoid Production of *Phaffia rhodozyma* in Fed-batch Cultures with Different Feeding Methods, Biotechnology Letters, vol. 21, pp. 175-178.*
Nishio et al. Journal of Fermentation Technology, 1977, vol. 55, pp. 151-155.*
Cutayar et al. Biotechnology Letters, 1989, vol. 11, No. 3, pp. 155-160.*
Nishio et al. "A Fed-Batch Culture of Methanol-utilizing Bacteria with pH Stat" Journal of Fermentation Technology, 1977, V55, p. 151-155.
Cutayar et al. "High Cell Density Culture of *E. coli* in a Fed-Batch System with Dissolved Oxygen as Substrate Feed . . ." Biotechnology Letters, 1989, V11, N3, p. 155-160.
Konstantinov et al., "A balanced DO-stat and its application to the control of acetic acid excretion by recombinant *Escherichia coli*," *Biotechnology and Bioengineering* 36 (1990) 750-758.
Lee, SY, "High cell-density culture of *Escherichia coli*," *Trends in Biotechnology* 14 (1996) 98-105.
Mori et al., "High density cultivation of biomass in fed-bath system with DO-stat," *Journal of Chemical Engineering of Japan 12* (1979) 313-319.
Suzuki et al., "Phenomenological background and some preliminary trials of automated substrate supply in pH-stat modal fed-batch culture using a setpoint of high limit," *Journal of Fermentation and Bioengineering* 69 (1990) 292-297.
Wong et al., "Effect of post-induction nutrient feeding strategies on the production of bioadhesive protein in *Escherichia coli*," *Biotechnology and Bioengineering* 60 (1998) 271-276.
International Search Report for PCT/US2004/044183 dated Jun. 15, 2004.
Abstract of JP 4234981A published Aug. 24, 1992 (Mitsui Toatsu Chemicals).

* cited by examiner

*Primary Examiner*—Jon Weber
*Assistant Examiner*—Kailash C Srivastava

(57) ABSTRACT

Embodiments of the present invention generally relate to novel fed-batch fermentations wherein processes of DO-stat and pH-stat are combined for nutrient feeding control.

13 Claims, 3 Drawing Sheets

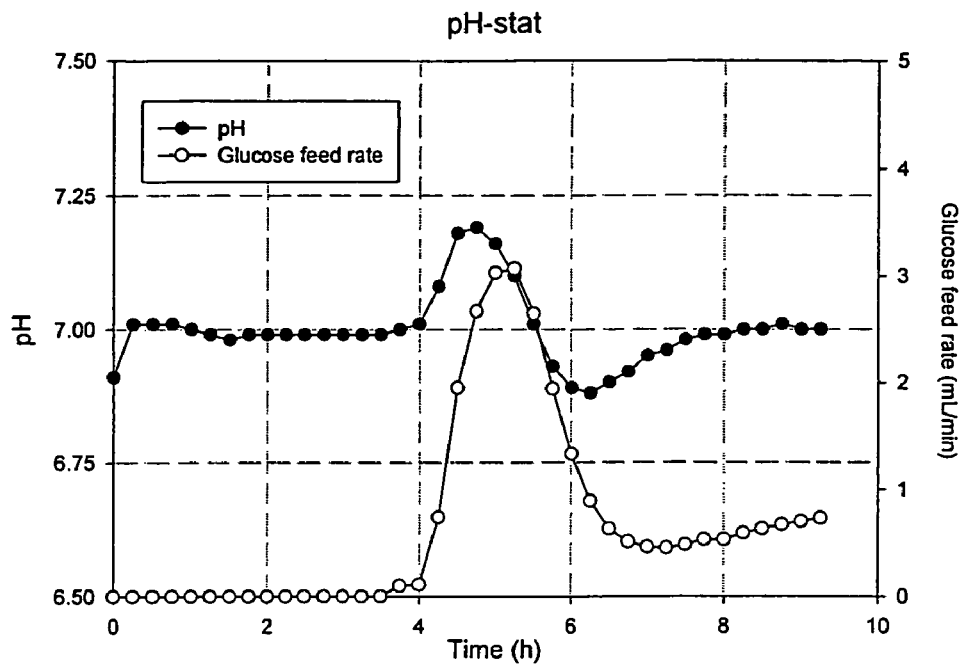
Figure 1 (Prior Art): pH and glucose feed rate profiles for the pH-stat control scheme
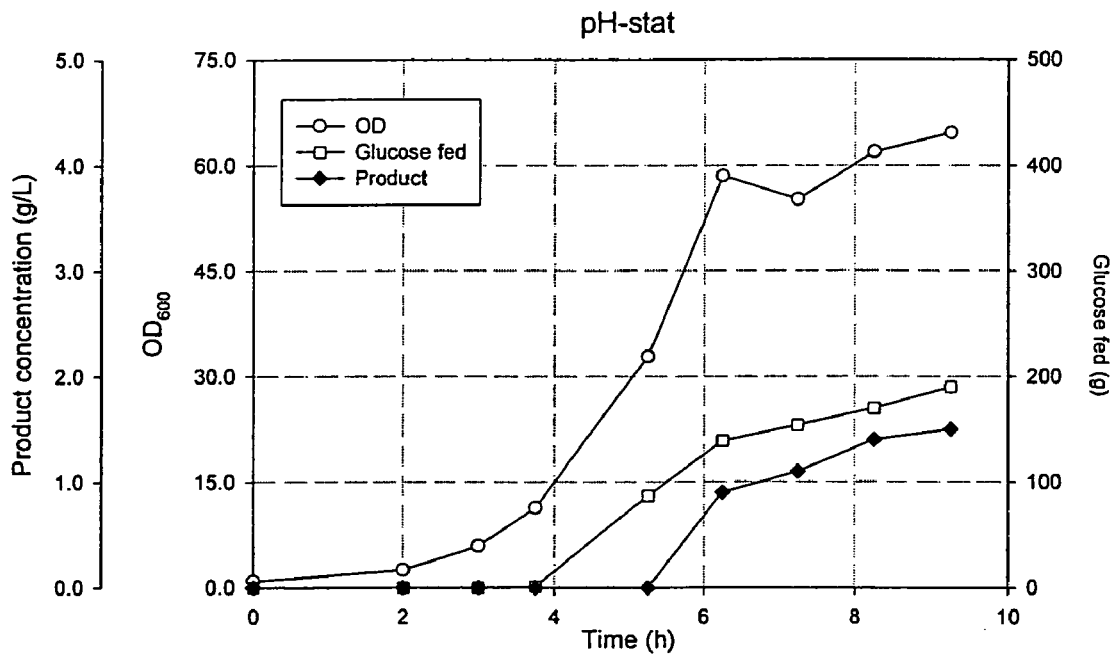
Figure 2 (Prior Art): Cell growth, glucose consumption, and product concentration profiles for the pH-stat control scheme

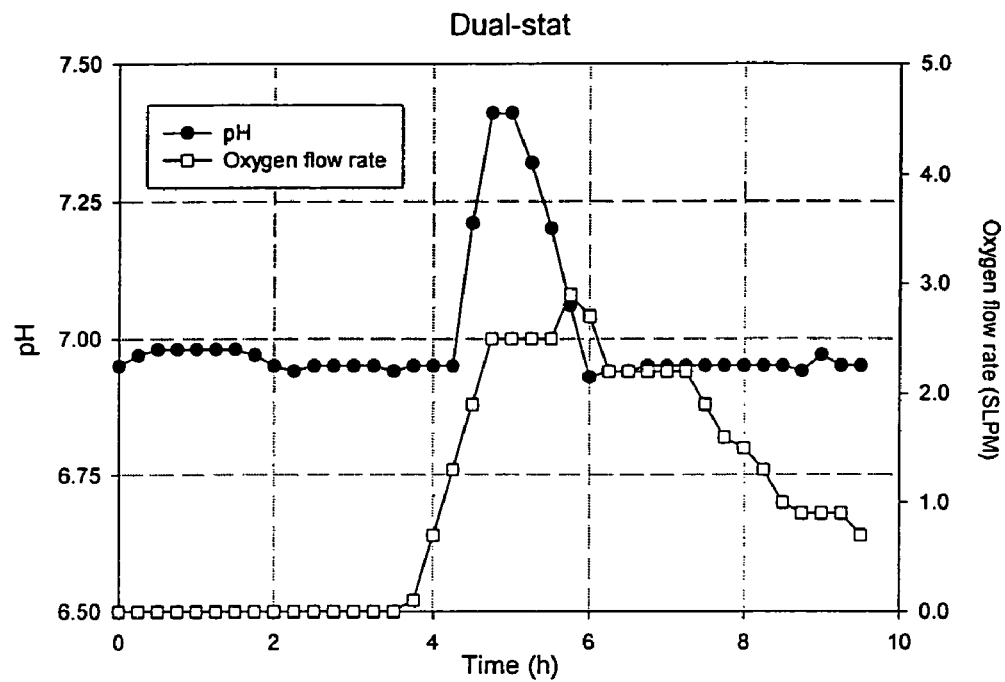
Figure 3: pH and oxygen flow rate profiles for the dual-stat control scheme
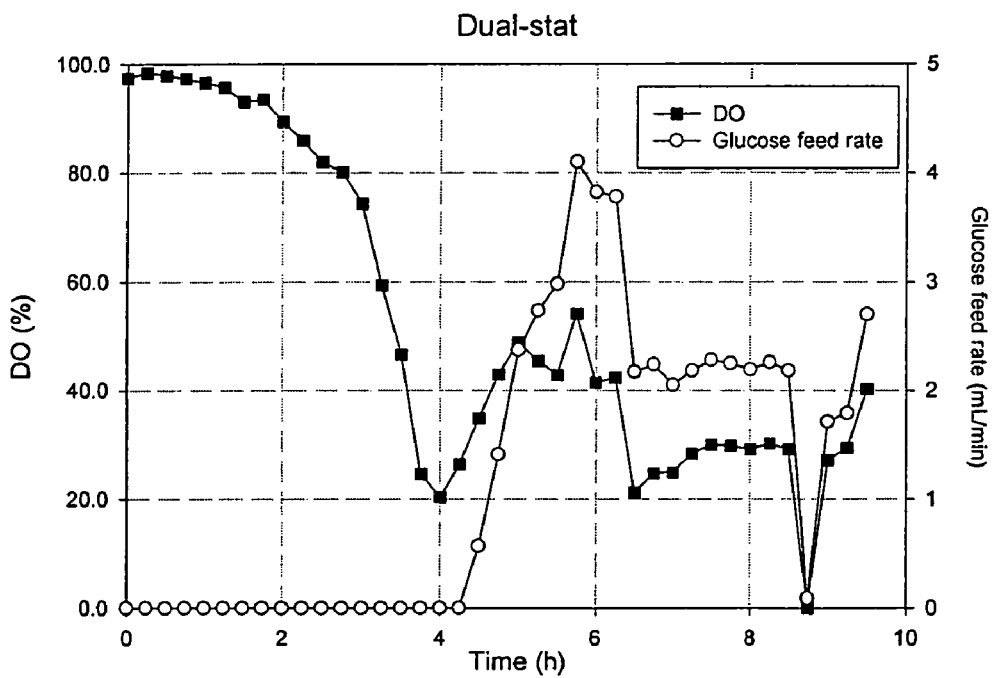
Figure 4: Dissolved oxygen (DO) and glucose feed rate profiles for the dual-stat control scheme

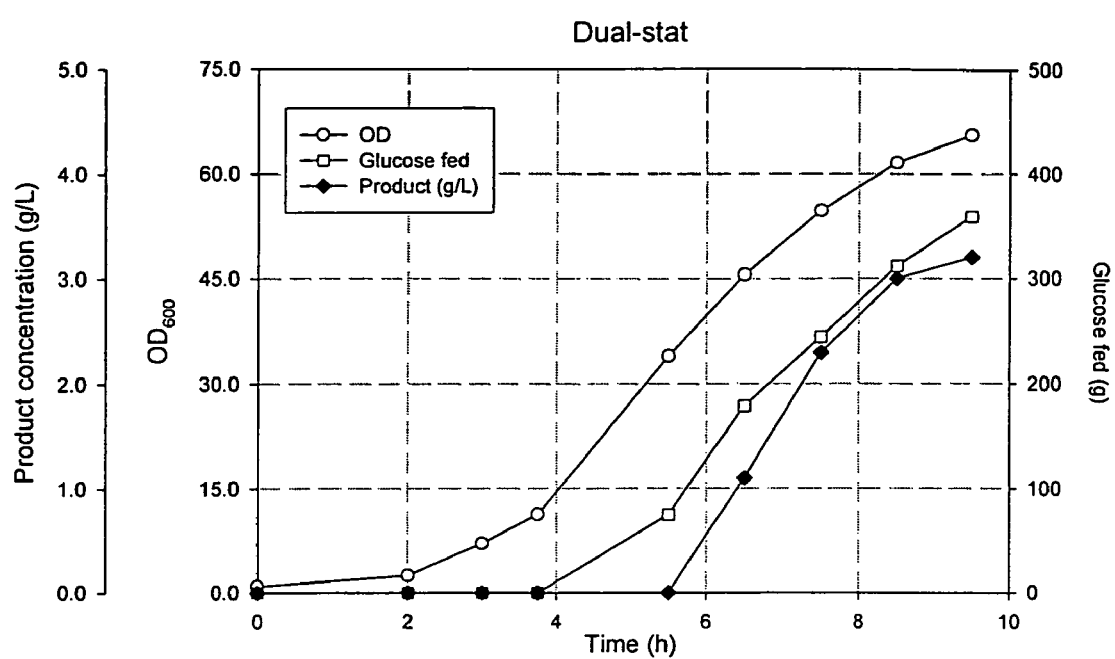
Figure 5: Cell growth, glucose consumption, and product concentration profiles for the dual-stat control scheme

FEEDING PROCESSES FOR FERMENTATION

RELATED APPLICATIONS

This Application is a divisional of application Ser. No. 10/292,064, filed Nov. 12, 2002, now U.S. Pat. No. 6,955,892.

FIELD OF THE INVENTION

Embodiments of the present invention generally relate to novel processes for fermentation.

BACKGROUND OF THE INVENTION

The Pharmaceutical Industry has produced compounds of interest through fermentative production for a very long time. Generally, in a fermentation production facility, a compound (or compounds) of interest, such as certain organic compounds, proteins, carbohydrates, and the like can be produced in large quantities by culturing cells (often referred to as "host cell(s)") in a liquid nutrient solution called medium. These host cells produce the compound(s) of interest either naturally or through genetic engineering or recombinant DNA technology.

In an embodiment, to culture the host cells, typically, the cells are submerged in a tank (often referred to as fermentor or bioreactor) of varying size containing a nutrient medium. This nutrient medium allows the cells to grow, multiply, and synthesize the compound(s) of interest. This process is often referred to as fermentation or cell culture. Harvesting the compound(s) of interest often requires extracting the compound(s) directly from the cells or from the supernatant.

Two commonly used fermentation systems are the continuous culture system and the fed-batch culture system, according to U.S. Pat. No. 5,639,658 to Drobish et al. The continuous culture system is typically used to extend the growth phase of the culture cells over long periods of time by providing fresh medium to the cells while simultaneously removing spent medium and cells from the fermentor. Such a culturing system serves to maintain optimal culturing conditions for certain host cell types and compounds of interest. The fed-batch fermentation system is generally defined as batch culture systems wherein fresh nutrients and/or other additives such as precursors to products are added as demanded by the fermentation process but no medium is withdrawn. There are three primary types of medium: chemically defined media, semi-defined media, and rich complex media.

A chemically defined medium as is illustrated in U.S. patent application Ser. No. 09/982,474, published on Apr. 4, 2002, is a medium essentially composed of chemically defined constituents. A semi-defined medium refers to a chemically defined medium supplemented with a small amount of complex nitrogen and/or carbon source(s), an amount as defined below, which typically is not sufficient to maintain growth of the micro-organism and/or the guarantee formation of a sufficient amount of biomass.

A rich complex medium is typically defined as a medium comprising a complex nitrogen and/or carbon source, such as soybean meal, cotton seed meal, corn steep liquor, yeast extract, casein hydrolysate, molasses, and the like. Likewise, a complex medium is a complete or nearly complete nutrient source for the microorganism. Rich complex media, in embodiments contain a carbon and a nitrogen source as well as vitamins, trace metals and minerals.

There are two primary types of fermentation: solid-state fermentation and aqueous fermentation. Solid-state fermentation includes the steps of cultivation of media, inoculation of the media with microorganisms, cultivation of the multi-organisms, extraction of biological products from the cultivated microorganisms and treatment of the waste materials from the culture. Solid-state fermentation is disclosed in U.S. Pat. No. 6,197,573 to Suryanarayan et al. Aqueous state fermentation is as disclosed below.

As is disclosed in U.S. Pat. No. 5,595,905 to Bishop et al, during a fermentation process, the bacteria or yeast growing in the fermentation broth consume nutrients at a variable rate. This rate is often related to such factors as the microorganism density and rate of growth. It is common in the fed-batch fermentation that the rate of consumption of nutrients will increase exponentially until an upper limit is reached for the fermentation that is often determined by the size of the fermentor or amount of nutrient and dissolved oxygen available in the medium.

As is disclosed in the prior art, it is desirable to maintain an adequate or sufficient concentration of nutrient in the medium. When the nutrient concentration is too high, either undesirable by-products, usually acetic acid, lactic acid or ethanol are produced, or growth inhibition is observed due to nutrient toxicity at higher concentrations[4]. When the nutrient concentration is too low the microorganism growth rate is restricted. Accordingly, the art field has strived to control the nutrient concentration in the medium. This is often involved different feeding patterns or measurements.

For example, in U.S. Pat. No. 5,595,905, patentees disclose taking samples from a culture medium, analyzing those samples, and based upon the analysis adding further nutrients to the water in an attempt to keep the nutrient concentration at constant in the culture. The '905 patent discloses using a computer to assist in monitoring the nutrient concentration.

U.S. Pat. No. 6,284,453 discloses general approaches to improving product formation that include, 1) using the best growth medium (carbon source, nitrogen source, precursors, and nutrients such as vitamins and minerals); 2) using the optimal pH, redox potential, agitation rate, aeration rate, ionic strength, osmotic pressure, water activity, hydrostatic pressure, and/or the like; 3) using the optimal dissolved oxygen or carbon dioxide concentration; 4) using inducers and repressors; 5) varying the above in a time-optimal fashion; 6) minimizing the accumulation of by-products that negatively impact the growth or metabolism of the organism, 7) genetically altering the organism using recombinant DNA or hybridoma technology; and, 8) using auxotrophic or mutants with altered regulatory systems, 9) and/or the like. Several methods have emerged to control growth and metabolism in a culture. As the '453 patent illustrates, various techniques use automated on-line or at-line measurements of the concentration of growth-limiting substrates such as glucose and glutamine. However, as can be imagined, feedback control based on substrate measurements can be relatively slow and less responsive. Likewise, another method that has met some success is to add growth-limiting substrate in an exponential manner. However, this exponential growth technique suffers from the drawbacks of allowing the culture medium to be underfed and/or overfed thereby not obtaining the optimal growth and metabolism characteristics. Another feedback measure of growth and metabolism is to measure the specific oxygen uptake rate and maintain it at a setpoint corresponding to the desired growth rate. This method is very effective in cultures with low growth rate. Another method is the dissolved oxygen-stat (DO-stat) method, which will be defined below. Likewise, another method includes pH-stat, which will also be defined below. Further methods include carbon dioxide transfer rate measurements, oxygen uptake measurements, respiratory quotient (RQ) measurements and the like. While these methods have proven successful under certain conditions, there are potential limitations associated with each method (see Table 1 for examples). Accordingly, the art field is in need of an improved measurement for monitoring and controlling the growth and metabolism characteristics of a culture.

The '453 patent discloses a novel method for controlling growth rate and metabolic state in a fed-batch fermentation by measuring the reagent addition rate, pH, oxygen uptake rate, biomass concentration, and reactor volume. The measurement of the reagent addition rate is divided by the measurement of the oxygen uptake rate and maintained at a predetermined setpoint. Another embodiment is disclosed where a reagent addition rate is divided by the product of the biomass concentration and the reactor volume and maintained at a setpoint corresponding to a desired growth rate. A further additional embodiment is disclosed wherein the reagent addition rate and a specific oxygen uptake rate are maintained at different setpoints corresponding to a desired growth metabolic rate. However, as can be seen, the process disclosed on the '453 patent requires numerous measurements and calculations, and may be difficult to implement in commercial production on a routine basis. Therefore, the art field is in need of a process whereby simple measurements may be taken without complex calculations resulting in optimal growth and metabolic characteristics.

It is common for high cell density microbial fermentations to use a fed-batch mode of operation in order to resolve issues such as metabolic by-product accumulation or substrate inhibition, equipment limitation, etc. Cells are typically grown in batch mode to an intermediate cell density following which feeding of carbon/energy and/or complex nutrients is initiated. The feeding strategies can be classified into two major categories: (1) open-loop (non-feedback) and (2) closed-loop (feedback) feeding strategies.

The open-loop feeding strategies are typically pre-determined feed profiles for carbon/nutrient addition. There are an infinite number of feed profiles, but more commonly the feed rates are either constant or increased feed rate (either constant, stepwise or exponential) in order to keep up with the increasing cell densities. While these simple pre-determined feed profiles have been applied successfully in certain cases, the major drawback is the lack of feed rate adjustment based on metabolic feedback from the culture. Therefore, the open-loop feeding strategies can fail if an unexpected disturbance causes the culture to deviate from its "expected" growth pattern.

The closed-loop feeding strategies, on the other hand, rely on a measurement that is an indicator of the metabolic state of the culture. Two most commonly measured online variables, the dissolved oxygen (DO) concentration and pH, in microbial fermentation are also key indicators of cellular physiology. Therefore, they have traditionally been used as feedback variables upon which the feed rates are based. These more sophisticated closed-loop feeding strategies, called DO-stat and pH-stat which are based on the measurement of DO and pH respectively, have been utilized to minimize accumulation of inhibitory metabolites, such as acetate, during high cell density cultivation[1,2,3].

The traditional DO-stat control of nutrient feeding is simply based on the concept of DO rises (due to a reduction or cessation of oxygen consumption or respiration) upon nutrient limitation or depletion. The DO-stat control maintains the culture at a constant DO level (the DO setpoint) by increasing the nutrient feed rate when DO rises above the setpoint and reducing the nutrient feed rate when DO drops below the setpoint. The DO-stat strategy typically works well in defined media where nutrient depletion results in rapid DO rise. However, the DO-stat method often fails in media supplemented with rich complex nutrients such as yeast extract, tryptone, peptone, casamino acid, or Hy-Soy. Rich complex nutrients are capable of supporting cellular maintenance and respiration through amino acid catabolism such that the DO level remains low (i.e. no apparent DO spikes) even under carbon source limitation or depletion.

When a complex medium is used for culture growth, a pH-stat strategy may be more suitable than DO-stat since the culture pH tends to increase once the carbon source is depleted. In a manner similar to DO-stat control, the pH-stat method maintains a constant culture pH at about the setpoint by increasing the nutrient feed rate as pH rises above the setpoint and reducing the nutrient feed rate when pH drops below the setpoint. However, since the change in culture pH upon nutrient depletion is less responsive than that of DO, feeding control by pH-stat can be relatively sluggish when compared to DO-stat. In addition, the pH-stat control does not work well for culture grown in chemically defined media[3,4].

As explained before, in general, when the carbon source becomes limiting or depleted in fermentations employing complex medium, the culture pH rises while the DO value remains low. This suggests an active respiration in the absence of primary carbon source. This pH rise upon carbon source depletion is due to a combination of metabolism shift (to utilizing complex nitrogen which releases hydroxide after ammonium uptake) as well as reutilization of excreted acids (such as acetic acid). Similarly, the low DO value during carbon source depletion is most likely due to the metabolism shift to utilizing amino acids from the complex nitrogen feed. The degradation products of amino acids enter the tricarboxylic acid (TCA) cycle (e.g., 2-oxoglutarate, a deaminated product of glutamate, is an intermediate of the TCA cycle) and maintain active aerobic respiration, which results in oxygen consumption and low DO profile even under glucose depletion. Clearly the DO-stat control will not function properly if the culture DO concentration remains low during glucose limitation.

Therefore, the art field is in search of an improved method that can take advantage of the benefits offered by both pH and DO-stat without the usual drawbacks.

SUMMARY OF THE INVENTION

Embodiments of the present invention generally relate to fermentation processes, fermentations, and fermentation compositions. In an embodiment, novel processes are disclosed for fed-batch and continuous fermentation. Generally, technologies of DO-stat and pH-stat are combined to control the feed rates of substrate or nutrient (primary carbon/energy source such as glucose and glycerol), sometimes referred to as nutrient, and enriched oxygen. In an embodiment, the substrate or nutrient (primary carbon/energy source) feed rate is controlled by a DO-stat. In an embodiment, the pH of a fermentation is maintained at about a setpoint (pH-stat) by adjusting the feed rate of enriched oxygen (which indirectly affect the substrate or nutrient (primary carbon/energy source) feed rate through DO-stat). In various embodiments, the pH of a fermentation can also be maintained at about a setpoint by adjusting agitation, aeration, back pressure, or a combination of these components in the fermentor. In further embodiment, a DO-stat and pH-stat are linked. In another embodiment, the linked DO-stat and pH-stat operate simultaneously to maintain the DO and pH of a fermentation at about a setpoint by adjusting the feed rate of substrate or nutrient (primary carbon/energy source) and the feed rate of enriched oxygen.

This summary is not intended to act as a limitation on the scope of the appended claims. For an understanding of the invention, attention should be had on the appended claims.

BRIEF DESCRIPTION OF THE FIGURES

FIG. 1 is a graph illustrating a plot of a prior art pH-stat fermentation feeding control wherein the pH and glucose feed rate of the fermentation are plotted against culture time.

FIG. 2 is a graph illustrating a plot of the prior art pH-stat fermentation feeding control of FIG. 1 wherein the cell growth (expressed as optical density, or OD), glucose consumption and product concentration of the fermentation are plotted against culture time.

FIG. 3 is a graph illustrating a plot of pH and enriched oxygen flow rates of a dual DO-pH stat control of an embodiment of the present invention plotted against culture time.

FIG. 4 is a graph illustrating the dissolved oxygen (DO) measurement and the glucose feed rate of a dual DO-pH stat control of the embodiment of FIG. 3 plotted against culture time.

FIG. 5 is an illustration of a graph of cell growth (OD), glucose consumption and product concentration of an embodiment of a dual DO-pH stat control of the embodiment of FIG. 3 plotted against culture time.

DETAILED DESCRIPTION OF THE INVENTION

As used herein, the term "nutrient" means and refers to nutrients or substrates that may be fed to a fermentation process, such as carbon/energy sources, such as glucose, carbohydrates, vitamins, minerals, oils, and the like. As used herein, the term "culture" shall mean and refer to at least one medium containing at least one microbial strain and the like which is suitable for fermentation, such as, but not limited to, fungal, yeast, and bacterial strains. It is to be understood that the term "culture" as used in the present invention includes a medium wherein all necessary components are added to the medium before the start of the fermentation process, and further includes a medium wherein part of the necessary components are added before starting and part are added to the medium during the fermentation process. As used herein, the term "dissolved oxygen content" shall mean and refer to the dissolved oxygen content of the medium and/or culture. As used herein, the term "medium" means and refers to a nutrient system for the artificial cultivation of cells, organisms, and/or the like. As used herein, the term "computer," means and refers to a programmable machine or other device that can store, retrieve, and process data.

The type of carbon, nitrogen and complex nitrogen source, which is used in the rich complex medium, is not critical to the invention. Preferably, a primary carbon source is selected from the group consisting of carbohydrates such as glucose, lactose, fructose, sucrose, maltodextrins, starch and inulin, glycerol, vegetable oils, hydrocarbons, alcohols such as methanol and ethanol, organic acids such as acetate and higher alkanoic acids. More preferably, a carbon source is selected from the group consisting of glucose, glycerol, lactose, fructose, sucrose and soybean oil. It is to be understood that the term "glucose" includes glucose syrups, i.e. glucose compositions containing glucose oligomers. Most preferred carbon sources comprise glucose, glycerol, other carbohydrates, and/or other nutrient solutions containing one or a combination of these sugars.

A defined nitrogen source preferably is selected from the group consisting of urea, ammonia, nitrate, ammonium salts (such as ammonium sulphate, ammonium phosphate, ammonium chloride and ammonium nitrate), and amino acids such as glutamate and lysine. More preferably, a nitrogen source is selected from the group consisting of ammonia, ammonium sulphate, ammonium chloride and ammonium phosphate. Most preferably, the nitrogen source is ammonia. The use of ammonia as a nitrogen source has the advantage that ammonia additionally can function as a pH-controlling agent. In case ammonium sulphate and/or ammonium phosphate are used as a nitrogen source, at least a portion of the sulphur and/or phosphorus requirement of the microorganism may be met.

A rich complex nitrogen source preferably is selected from the group consisting of one or more of the following components: yeast extract, yeast autolysates, yeast nitrogen base, protein hydrolysates (including, but not limited to, peptones, casein hydrolysates such as tryptone and casamino acids), soybean meal, Hy-Soy, tryptic soy broth, cotton seed meal, malt extract, corn steep liquor, molasses, and the like. More preferably, the complex nitrogen source is selected from the group consisting of yeast extract, tryptone, casamino acids, peptone, casein hydrolysate and Hy-Soy. Most preferably, the complex nitrogen source is yeast extract and/or tryptone.

Accordingly, in varying embodiments, the medium comprises one or more of the following: glucose, yeast extract, potassium phosphate monobasic, sodium phosphate dibasic, ammonium sulfate, magnesium sulfate, calcium chloride, thiamine, kanamycin sulfate, antifoam and trace elements (including zinc sulfate, ferric chloride, manganese chloride, cupric sulfate, cobalt chloride, sodium molybdate and boric acid).

In varying embodiments of the present invention, to resolve the problems associated with DO-stat or pH-stat control strategies in microbial fermentations employing complex medium, a new substrate or nutrient (or primary carbon/ energy source) feeding strategy was developed. The new strategy, called the DO-pH dual-stat, utilizes both DO-stat and pH-stat methodologies simultaneously to control the carbon/energy source feed via DO-stat by supplementing the culture with enriched oxygen to maintain the culture pH constant at about the setpoint. As the culture pH rises above the setpoint due to carbon/energy source (such as glucose) depletion, the supplemental oxygen flow rate is increased (via either manual or automatic control) to elevate the culture DO level. This rise in culture DO results in an increase in carbon source feed rate (which is under DO-stat control) such that the acidic by-products (as an example, but not limited to, acetate) generated through metabolism of the carbon/energy source balance the generation of ammonium, or other base, from the utilization of complex nitrogen sources. Thus, the culture pH is maintained at about its setpoint by controlling an enriched oxygen feed rate (under pH-stat control) that indirectly controls the carbon/energy source feed rate (under DO-stat control). In various embodiments, the enriched oxygen feed (that is under pH-stat control) may be substituted by agitation, aeration, fermentor back pressure, or a combination of these components. In another embodiment, the carbon/energy source (such as glucose) feed rate is proportional to the dissolved oxygen content in the fermentation. In further embodiment, this unique DO-pH dual-stat strategy provides a well-balanced nutrient feed control. In other words, the dual-stat's feed-on-demand approach, which is based on the feedback of culture pH and dissolved oxygen, essentially eliminates (or minimizes) the typical drawbacks encountered in other types of feeding strategies, such as excessive by-product accumulation and reduced growth rate due to overfeeding or underfeeding, thereby enhancing the efficiency of the fermentation. An additional advantage of the present invention is that it does not require any at-line or off-line measurement of growth-limiting substrates or metabolites. It is based on the feedback of real-time DO and pH on-line measurements through standard DO and pH probes.

In general, processes of the present invention comprise the step of maintaining a pH of a fermentation medium at about a setpoint by controlling oxygen feed, and/or agitation, aeration, back pressure, or a combination of these components. In varying embodiments, controlling oxygen feed (and/or agitation, aeration, back pressure, or a combination of these components) indirectly controls a nutrient feed rate (carbon/energy source feed rate). Further, the oxygen feed may have any content/percentage oxygen, such as air, enriched oxygen, pure oxygen, and/or any concentration thereof. The oxygen feed to the fermentation may be from one source and/or inlet or through multiple sources and/or inlets. Oxygen feed may be controlled by manners common in the art, such as by controlling the oxygen feed rate.

Processes of the present invention may be used in any fermentation or cell culture. In preferred embodiments, the fermentation is a fed-batch, continuous, and/or combination of these employing rich complex nutrients.

In various embodiments, the oxygen feed rate (and/or agitation, aeration, back pressure, or a combination of these components) of the fermentation is controlled by a pH-stat. In further embodiment, the feed rate of carbon/energy source is about proportional to the dissolved oxygen content (i.e., DO-stat). However, in other embodiments, the enriched oxygen feed can also be controlled manually (instead of under pH-stat control). For example, a constant oxygen feed rate may be used as long as the enriched oxygen flow rate is maintained at a sufficient level such that the glucose feed rate (under DO-stat control) is high enough to prevent culture pH from rising. A rise in culture pH (excluding the case of base addition) typically relates to metabolism shift from primary carbon/energy source to complex nitrogen (or other secondary carbon/energy sources such as amino acids) due to underfeeding of primary carbon/energy source(s). In other embodiments, the primary carbon/energy source (e.g., glucose) feed rate may be other than proportional and may have no comparable relation to the dissolved oxygen content.

In various embodiments, the fermentation can be manually controlled or automated by a computer or other machine. In an embodiment, the pH is monitored on a computer. In further embodiment, a computer and/or computer aided device controls and/or adjusts an oxygen feed rate (and/or agitation, aeration, back pressure, or a combination of these components) to maintain the pH at about a setpoint. Further embodiments monitor the dissolved oxygen content with a computer and/or computer aided device. The use of computer in this application is specifically intended to include all necessary programs, controllers, devices and/or the like to function as claimed and/or described.

In certain preferred embodiments, the computer or the computer aided device or other computer or computer aided device controls the substrate or nutrient (primary carbon/energy source) feed rate in relation to the dissolved oxygen content, such as with a DO-stat. In a most preferred embodiment, the substrate or nutrient (primary carbon/energy source) feed rate is proportional to the error between the DO content reading and the DO setpoint, and is controlled to maintain the DO level at about a setpoint.

Accordingly, the present invention comprises the steps of: maintaining a pH of a fermentation medium at about a setpoint by controlling an oxygen feed rate which indirectly controls a nutrient feed rate. In an embodiment, the fermentation process is fed-batch fermentation. In other embodiments, the fermentation process is continuous fermentation.

Embodiments of the present invention also envision an apparatus and/or fermentor. In various embodiments, the fermentation comprises a fermentor, multiple nutrient feeds including substrate or nutrient (primary carbon/energy source such as glucose) feed and rich complex nitrogen feed (such as yeast extract solution), a fermentation batch medium, base, air and oxygen feed. The pH of the fermentation is maintained at about a setpoint by adjusting the oxygen feed rate (and/or agitation, aeration, back pressure, or a combination of these components), which indirectly controls the feed rate of substrate or nutrient (primary carbon/energy source) to the medium. Further embodiments comprise a pH-stat and/or a DO-stat, whereby the oxygen feed rate (and/or agitation, aeration, back pressure, or a combination of these components) is controlled by the pH-stat and the substrate or nutrient (primary carbon/energy source) feed rate is controlled by the DO-stat.

In another embodiment, the present invention envisions a fermentation apparatus comprising: a fermentor, a nutrient feed, a rich complex nitrogen feed, a fermentation batch medium, a base feed, an air feed, and an oxygen feed wherein the pH of the fermentation is maintained at about a setpoint by controlling an oxygen feed rate which indirectly controls a nutrient feed rate to a culture. The apparatus may be modified, in an embodiment, such that the fermentation apparatus further comprises a pH-stat, whereby at least one of the oxygen feed rate, agitation, aeration, fermentor back pressure, or a combination of these components is controlled by the pH-stat. Further embodiments comprise a DO-stat, whereby the nutrient feed rate is controlled by the DO-stat. Other embodiments further comprise a computer, whereby the computer controls the pH-stat and/or the DO-stat.

EXAMPLES

Table 1 demonstrate a general performances of the DO-pH dual-stat when compared to the performance of a pH-stat, open-loop and DO-stat control for a recombinant *E. coli* fermentation, the process for which is well known in the art.

TABLE 1

Comparison of different feeding strategies in fermentation

| Feeding strategy | Open-loop | DO-stat | pH-stat | DO-pH Dual-stat |
|---|---|---|---|---|
| Defined Media | + | + (fast response) | – (slow response) | + (fast response) |
| Rich Complex Media | + | – (may not work) | +/– (slower response; metabolic shift) | + (fast response) |
| Metabolic Feedback | no (predetermined) | yes | Yes | Yes |

*The symbols "+" and "–" indicate the relative status of good vs. poor performance when various feeding strategies are applied in different media.

As can be seen, when compared to the traditional feeding strategies described earlier (open-loop, standard DO-stat, and pH-stat), features of the dual-stat strategy are:

1. The new DO-pH dual-stat feeding strategy works well in culture(s) supplemented with rich complex nutrients while the DO-stat may not function well, and that pH-stat alone shows typical slow response;

2. The new DO-pH dual-stat feeding strategy will also work well for culture(s) grown in defined media whereas a pH-stat may not;
3. The new DO-pH dual-stat feeding strategy retains the advantages of fast responsiveness and metabolic feedback control in both defined media and complex media;
4. The new DO-pH dual-stat control strategy does not require any at-line or off-line measurement of growth-limiting substrates or metabolites. It is based on the feedback of real-time DO and pH on-line measurements through standard DO and pH probes;
5. The new DO-pH dual-stat feeding methodology can also be applied to non-microbial cultivation(s) such as animal or insect cell culture(s).

The data illustrated in the figures have been derived from fermentation runs with a pH-stat and a DO-pH dual-stat, as indicated by the figure.

Experimental conditions of the following runs were as follows:

A 2.8-L shake flask containing 1,000±50 mL of LB seed medium (with 30±5 mg/L kanamycin sulfate) was inoculated with 50±2 µL stock culture from a Development Cell Bank vial (*Escherichia coli* strain BLR(DE3) expressing a recombinant protein). The seed flask was incubated at 37.0±1.0° C., 200±20 RPM until the $OD_{600}$ reached 1 to 4. This culture was used to inoculate a 15-L production fermentor (10-L typical working volume) containing 8.0±0.5 L production medium supplemented with 30±5 mg/L kanamycin sulfate.

The production medium contained the following components: glucose, yeast extract, potassium phosphate monobasic, sodium phosphate dibasic, ammonium sulfate, magnesium sulfate, calcium chloride, thiamine, kanamycin sulfate, antifoam and trace elements (including zinc sulfate, ferric chloride, manganese chloride, cupric sulfate, cobalt chloride, sodium molybdate and boric acid).

The fermentation process was controlled at 37.0±1.0° C. and pH 7.0±0.3 (with ammonia hydroxide) for about 9 to 12 h. Airflow was kept constant at 8.0±1.0 SLPM throughout. The dissolved oxygen (DO) was maintained at about 30% saturation (preferably above 10% saturation) either by a constant agitation at 1000 RPM throughout; or by continuously increasing the agitation rate from 300 to 1,000 RPM (variable agitation mode). In the variable agitation mode, upon reaching the maximum agitation rate (1,000 RPM) the agitation control was switched to a manual constant 1,000 RPM for the rest of cultivation. Any further demand for dissolved oxygen was met by supplementary enriched oxygen in the range of 0.0 to 5.0 SLPM. When the $OD_{600}$ was 8 to 15, a 20% (w/v) yeast extract solution was fed to the fermentor at 2.0±0.5 g/min constant rate. When the residual glucose concentration was depleted (as indicated by a pH rise as well as glucose analyzer reading), a 50% (w/v) glucose feed, under the DO-pH dual-stat control (DO setpoint at 30% saturation), was activated. When the $OD_{600}$ reached 30 to 40 (about 5 to 8 hours elapsed fermentation time), the culture was induced for recombinant protein production by adding Isopropyl β-D-1-thiogalactopyranoside (IPTG) to a final concentration between 10 and 15 mM.

Three to four hours after induction, with an $OD_{600}$ 50 to 70, the fermentation culture was ready for cooling and subsequent harvest. Total fermentation time was typically 9 to 12 hours.

Now referring to FIG. 1, under the prior art pH-stat control scheme, as the pH of the fermentation increased above the setpoint (pH 7.0), the glucose feed rate increased. However, due to a slower pH response, the glucose feed rate was shown to be oscillating. Oscillation in pH and glucose feed rate results in a cycling of overfeeding and underfeeding of glucose to the culture, which leads to suboptimal growth conditions, lower product yield and/or increased operating costs.

It can be seen in FIG. 2 that between h 6 and h 8 elapsed time, the rates of cell growth and product formation decreased as a result of reduced glucose feed. Under the condition of glucose underfeeding in pH-stat control, the final product yield was only half of that in a dual-stat control process (see FIG. 5). Likewise, this process is not optimized.

In contrast, the pH and oxygen feed rate in a DO-pH dual-stat fermentation did not exhibit any oscillation (shown in FIG. 3), nor did the glucose feed rate (see FIG. 4). Under DO-pH dual-stat control, the glucose feed rate during induction phase (between approximately h 6 and h 9 elapsed time) was more than twice (about 2 mL/min; FIG. 4) of that under pH-stat control (less than 1 mL/min; see FIG. 1). In both pH-stat and DO-pH dual-stat processes, the glucose concentration in the culture remained below about 0.1 g/L throughout the entire feeding period (data not shown).

Now referring to FIG. 5, it can be observed that measurements of embodiments of the present invention produce optimized cell growth and product concentration. A comparison of FIG. 2 and FIG. 5 illustrates that an embodiment of a DO-pH dual-stat of FIG. 5 allows steady cell growth and dramatically increases the same product concentration. As can be seen, in FIG. 5, product concentration was maximized at the end of the run to above 3.0 g/L. FIG. 2 maximized product concentration at the end of the run to about 1.5 g/L. Therefore, the novel process of the present invention nearly about doubled final product concentration in the compared runs.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims. Such further and other embodiments are contemplated whereby additions of an acid and/or a base may be made to the fermentation. Further, all patents mentioned herein are hereby incorporated by reference.

REFERENCES

1. Mori, H., Yano., T., Kobayashi, T. and Shimizu, S. (1979). High density cultivation of biomass in fed-batch system with DO-stat. *Journal of Chemical Engineering of Japan*, 12(4), 313-319.
2. Konstantinov, K., Kishimoto, M., Seki, T. and Yoshida, T. (1990). A balanced DO-stat and its application to the control of acetic acid excretion by recombinant *Escherichia coli*. *Biotechnology and Bioengineering*, 36, 750-758.
3. Suzuki, T., Yamane, T. and Shimizu, S. (1990). Phenomenological background and some preliminary trials of automated substrate supply in pH-stat modal fed-batch culture using a setpoint of high limit. *Journal of Fermentation and Bioengineering*, 69(5), 292-297.
4. Lee, S. Y. (1996). High cell-density culture of *Escherichia coli*. *Trends in Biotechnology*, 14, 98-105.
5. Wong, H. H., Kim, Y. C., Lee, S. Y. and Chang, H. N. (1998). Effect of post-induction nutrient feeding strategies on the production of bioadhesive protein in *Escherichia coli*. *Biotechnology and Bioengineering*, 60, 271-276.

What is claimed is:

1. A process for conducting fermentation comprising a control strategy with an integrated pH-stat and a DO-stat comprising the step of:

maintaining a pH of a fermentation medium at about a setpoint by controlling an oxygen feed rate which indirectly controls a nutrient feed rate, wherein the oxygen feed rate is controlled by a pH-stat and the nutrient feed rate is controlled by a DO stat, wherein the nutrient feed rate is proportional to the difference between the DO content and the DO setpoint and the nutrient feed rate increases when the culture dissolved oxygen is above the setpoint or decreases as the dissolved oxygen is below the setpoint, and wherein the pH of the fermentation is monitored on a computer.

2. The process of claim 1, wherein the fermentation process is fedbatch fermentation.

3. The process of claim 1, wherein the fermentation process is continuous fermentation.

4. The process of claim 1, further comprising adding a rich complex nitrogen feed to the fermentation medium.

5. The process of claim 1, further comprising adding a base.

6. The process of claim 1, further comprising adding air and/or enriched oxygen feed.

7. The process of claim 1, wherein the nutrient is selected from the group consisting of glucose, glycerol, other carbohydrates, and other nutrient solutions containing one or a combination of these sugars.

8. The process of claim 1, wherein the computer performs the step of controlling the oxygen feed rate to maintain the pH at about a setpoint.

9. The process of claim 1, wherein a pH-stat controls the oxygen feed rate, agitation, aeration, fermentor back pressure, or a combination of these components.

10. The process of claim 1, wherein the computer controls the nutrient feed rate in relation to the dissolved oxygen content as with a DO stat.

11. The process of claim 1, wherein the medium is selected from the group consisting of a defined medium, semi-defined medium, and a rich complex medium.

12. The process of claim 1, whereby the oxygen feed rate is constant at a rate sufficient to prevent culture pH from rising.

13. The process of claim 1, wherein the oxygen or air feed rate is constant at 0.0 to 5.0 SLPM to prevent culture pH from rising.

* * * * *

UNITED STATES PATENT AND TRADEMARK OFFICE
CERTIFICATE OF CORRECTION

| | | |
|---|---|---|
| PATENT NO. | : 7,521,203 B2 | Page 1 of 1 |
| APPLICATION NO. | : 11/123715 | |
| DATED | : April 21, 2009 | |
| INVENTOR(S) | : Lin et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 612 days.

Signed and Sealed this

Twenty-first Day of September, 2010

David J. Kappos
*Director of the United States Patent and Trademark Office*